(12) United States Patent
Katou et al.

(10) Patent No.: US 9,939,520 B2
(45) Date of Patent: Apr. 10, 2018

(54) ULTRASOUND DIAGNOSTIC DEVICE WITH COHERENCE FACTOR CORRECTION

(75) Inventors: Yoshiki Katou, Tokyo (JP); Kenji Suzuki, Tokyo (JP)

(73) Assignee: KONICA MINOLTA MEDICAL & GRAPHIC, INC., Tokyo (JP)

(*) Notice: Subject to any disclaimer, the term of this patent is extended or adjusted under 35 U.S.C. 154(b) by 1517 days.

(21) Appl. No.: 13/452,004

(22) Filed: Apr. 20, 2012

(65) Prior Publication Data

US 2012/0277589 A1 Nov. 1, 2012

(30) Foreign Application Priority Data

Apr. 28, 2011 (JP) ................................. 2011-100579

(51) Int. Cl.
*A61B 8/00* (2006.01)
*G01S 7/52* (2006.01)
(Continued)

(52) U.S. Cl.
CPC ........ *G01S 7/52049* (2013.01); *A61B 8/4405* (2013.01); *A61B 8/4488* (2013.01); *A61B 8/5207* (2013.01); *A61B 8/5269* (2013.01); *A61B 8/587* (2013.01); *G01S 7/5205* (2013.01); *G01S 7/52077* (2013.01); *G01S 15/8915* (2013.01); *G10K 11/341* (2013.01)

(58) Field of Classification Search
CPC combination set(s) only.
See application file for complete search history.

(56) References Cited

U.S. PATENT DOCUMENTS 5,910,115 A * 6/1999 Rigby .................... G03B 42/06
600/443
7,744,532 B2 * 6/2010 Ustuner et al. ............... 600/437
(Continued)

FOREIGN PATENT DOCUMENTS

JP  11151241 A  6/1999
JP  2006204923 A  8/2006

OTHER PUBLICATIONS

Japanese Office Action dated Dec. 9, 2014, issued in counterpart Japanese Application No. 2011-100579.
(Continued)

*Primary Examiner* — Michael Kahelin
*Assistant Examiner* — Helene Bor
(74) *Attorney, Agent, or Firm* — Holtz, Holtz & Volek PC

(57) ABSTRACT

An ultrasound diagnostic device includes: an ultrasound probe which transmits ultrasound toward a tested subject by a plurality of transducers and obtains a received signal; a beam forming section for adding the received signal for each of the transducers with matching a phase of the received signal; an image processing section which generates an image data; a coherent factor calculation section which calculates a coherent factor which represents a ratio of a coherent sum to an incoherent sum; a coherent factor correction section which corrects the coherent factor so as not to be smaller than a predetermined value; and a signal correction section which correct the received signal after having been subject to the adding, by multiplying the received signal after having been subject to the adding by the coherent factor corrected by the coherent factor correction section as a coefficient.

15 Claims, 14 Drawing Sheets

(51) Int. Cl.
    *A61B 8/08*          (2006.01)
    *G01S 15/89*        (2006.01)
    *G10K 11/34*       (2006.01)

(56) References Cited

U.S. PATENT DOCUMENTS

| | | | |
|---|---|---|---|
| 2005/0033165 A1* | 2/2005 | Ustuner et al. | 600/437 |
| 2005/0228279 A1* | 10/2005 | Ustuner | G01S 15/8927 |
| | | | 600/443 |
| 2006/0079780 A1* | 4/2006 | Karasawa | 600/447 |
| 2006/0173313 A1* | 8/2006 | Liu | G01S 7/52046 |
| | | | 600/437 |
| 2009/0141957 A1* | 6/2009 | Yen et al. | 382/131 |

OTHER PUBLICATIONS

Pai-Chi Li et al; Adaptive Imaging Using the Generalized Coherence Factor; IEEE Transactions on Ultrasonics, Ferroelectrics and Frequency Control, vol. 50, No. 2, Feb. 2003.

\* cited by examiner

ULTRASOUND DIAGNOSTIC DEVICE WITH COHERENCE FACTOR CORRECTION

This application is based on Japanese Patent Application No. 2011-100579 filed on Apr. 28, 2011, in Japan Patent Office, the entire content of which is hereby incorporated by reference.

TECHNICAL FIELD

The present invention relates to an ultrasound diagnostic device.

BACKGROUND

Conventionally, there have been known ultrasound diagnostic devices in which an oscillating probe having a large number of arrayed transducers is provided; ultrasound is transmitted to and received from a tested subject such as a living body; and on the basis of a signal having been obtained from received ultrasound, ultrasound image data is produced to display an ultrasound image based thereon on an image display device.

In such ultrasound diagnostic devices, ultrasound having been reflected from the same reflection object in electronic scanning has different arrival time with respect to each transducer due to transducer arrangement. In the conventional ultrasound diagnostic device, to correct this arrival time lag, ultrasound having been received with respect to each transducer is converted as an electronic signal, followed by beam forming processing to produce a signal for image formation. This beam forming processing is to adjust the time lag of each signal in which based on the geometric focal distances of transducers, delay correction is carried out for a delay amount having been set with respect to each transducer (each channel).

According to the conventional ultrasound diagnostic device, ideally, the same signal is expected to be obtained from every channel However, the acoustic velocity of ultrasound in a tested subject is not always constant, and actual delay amount may differ from the theoretical value. Therefore, all signals are not always subjected to correct beam forming. Thereby, image data with low S/N is eventually produced.

In view of such problems, a method to determine coherence factor as an indicator showing the quality of a signal having been subjected to beam forming is proposed. This coherence factor is calculated by the ratio of coherent sum to incoherent sum. An increase in this value indicates an excellent quality signal having been subjected to almost ideal beam forming. In contract, a decrease in the value indicates a poor quality signal in which in beam forming, a substantial error has been generated. Then, a thus-obtained coherence factor is applied to a signal having been subjected to beam forming and thereby weighing based on signal quality can be realized to produce image data in which artifacts are suppressed and S/N is enhanced (for example, Pai-Chi Li and Meng-Lin Li, Adaptive Imaging Using the Generalized Coherence Factor, IEEE Transactions on Ultrasonics, Ferroelectrics, and Frequency Control, Vol. 50 (2003), No. 2, pp. 128-141).

However, when weighing using a coherent factor is merely carried out to produce image data, for example, in a portion where an artifact such as sidelobe or speckle has emerged, weighed amount is locally minimized and thereby a so-called black defect is generated and then an unnatural ultrasound image may be shown. Thereby, a misdiagnosis by the reader may result and in some occasions, an inappropriate ultrasound image is eventually obtained.

In contrast, in the conventional ultrasound diagnostic device, there is proposed one in which feedback is performed so that the above coherence factor shows a more ideal value to adjust the delay amount per channel during transmission and reception (for example, U.S. Patent Application Publication No. 2005/0228279 specification).

However, in the technique described in U.S. Patent Application Publication No. 2005/0228279 specification, using a coherence factor, excellent quality image data of enhanced S/N can be produced but a circuit structure to adjust the delay amount per channel is required, resulting in an extremely complicated structure.

An object of the present invention is to provide an ultrasound diagnostic device in which, with a simple configuration, image data in which black defects are reduced and S/N is improved can be produced.

SUMMARY OF THE INVENTION

In view of the problems described above, it is an object of the present invention to provide an ultrasound diagnostic device comprising: an ultrasound probe which transmits ultrasound toward a tested subject by a plurality of transducers by a driving signal and obtains a received signal for each of the transducers by receiving a reflective ultrasound wave from the tested subject; a beam forming section for adding processing the received signal for each of the transducers with matching a phase of the received signal; an image processing section which generates an image data for displaying an ultrasound diagnostic image based on the received signal after having been subject to the adding; a coherent factor calculation section which calculates a coherent factor which represents a ratio of a coherent sum to an incoherent sum, based on the received signal obtained by the plurality of transducers; a coherent factor correction section which corrects the coherent factor calculated by the coherent factor calculation section so as not to be smaller than a predetermined value; and a signal correction section which correct the received signal after having been subject to the adding, by multiplying the received signal after having been subject to the adding by the coherent factor corrected by the coherent factor correction section as a coefficient.

It is preferable that, in the ultrasound diagnostic device, the coherent factor calculation section calculates the coherent factor CF(t) by the following expression (1):

$$CF(t) = \frac{\left|\sum_i C_i(t+\Delta t_i)\right|^2}{N\sum_i |C_i(t+\Delta t_i)|^2} \quad (1)$$

where N represents a number of the plurality of transducers and is a positive integer number;

t represents an arbitrary reference time;

i represents a channel of one arbitrary transducer among the N number of transducers;

$\Delta t_i$ represents a delay amount determined for the channel i; and $C_i(t+\Delta t_i)$ represents a received signal at a time obtained by adding the time t with the delay $\Delta t_i$.

It is preferable that in the ultrasound diagnostic device, the coherent factor correction section includes a limiter section which, when the coherent factor is less than the predetermined value, corrects the coherent factor to the predetermined value.

It is preferable that in the ultrasound diagnostic device, the coherence factor correction section includes a coherence factor conversion section which inputs the coherence factor and corrects the coherent factor so as to obtain an output value corresponding to the input coherent factor. And further it is preferable that the coherence factor conversion section obtains the output value by exponentiating the input coherent factor by a value γ which satisfies the following conditional expression: 0<γ<1.

PREFERRED EMBODIMENT OF THE INVENTION

An ultrasound diagnostic device according to a preferred embodiment of the present invention will now be described with reference to the drawings. However, the scope of the invention is not limited to the illustrated examples. Incidentally, in the following description, the same symbols will be assigned to those having the same function and configuration and then description thereon will be omitted.

Figure 1:
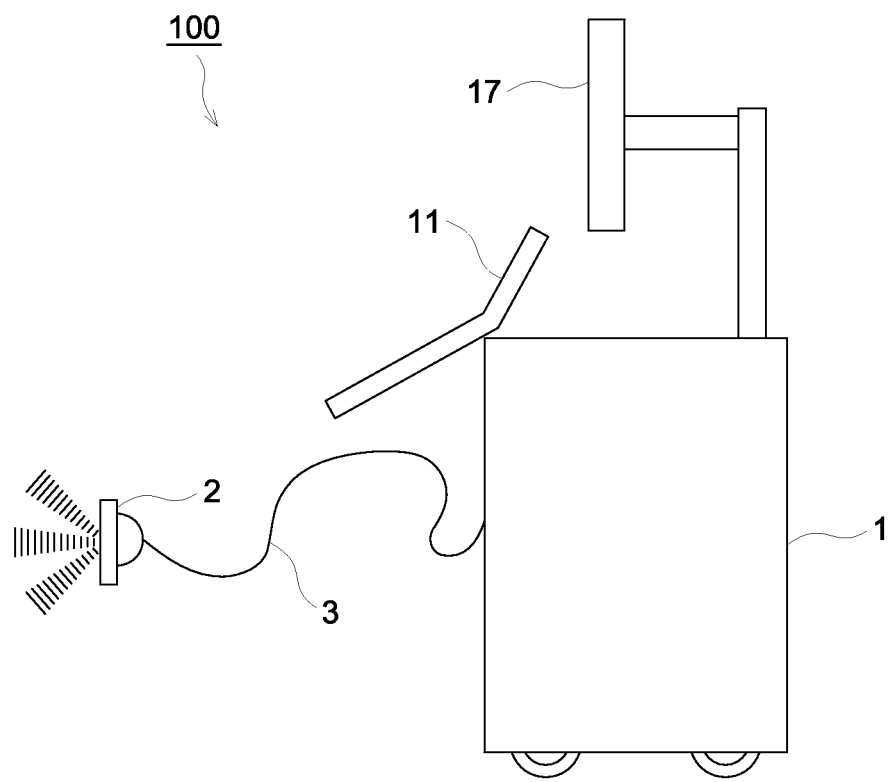
FIG. 1 is a view showing the exterior configuration of an ultrasound diagnostic device.

An ultrasound diagnostic device 100 according to the preferred embodiment of the present invention is provided with an ultrasound diagnostic device main body 1 and an ultrasound probe 2 as shown in FIG. 1. The ultrasound probe 2 transmits ultrasound (transmission ultrasound) to an unshown tested subject such as a living body and also receives a reflective wave of ultrasound having been reflected by this tested subject (reflection ultrasound: echo). The ultrasound diagnostic device main body 1 is connected to the ultrasound probe 2 via a cable 3, sending a drive signal being an electrical signal to the ultrasound probe 2 to allow the ultrasound probe 2 to transmit transmission ultrasound to a tested subject, as well as carrying out imaging of the interior state inside the tested subject, as an ultrasound image, based on a received signal being an electrical signal produced by the ultrasound probe 2 in accordance with reflection ultrasound from the interior of the tested subject having been received by the ultrasound probe 2.

The ultrasound probe 2 is provided with a transducer 2a containing a piezoelectric element. A plurality of the above transducers 2a are arranged, for example, in a one-dimensional array manner, in the azimuth direction (scanning direction). In the present embodiment, for example, an ultrasound probe 2 provided with 192 transducers 2a is used. Herein, the transducers 2a may be arranged in a two-dimensional array manner. Further, the number of the transducers 2a can be set appropriately. Still further, in the present embodiment, for the ultrasound probe 2, a linear electron scan probe was employed but any of an electron scanning type and a mechanical scanning type is employable. And, any of a linear scanning type, a sector scanning type, and a convex scanning type may also be employed.

Figure 2:
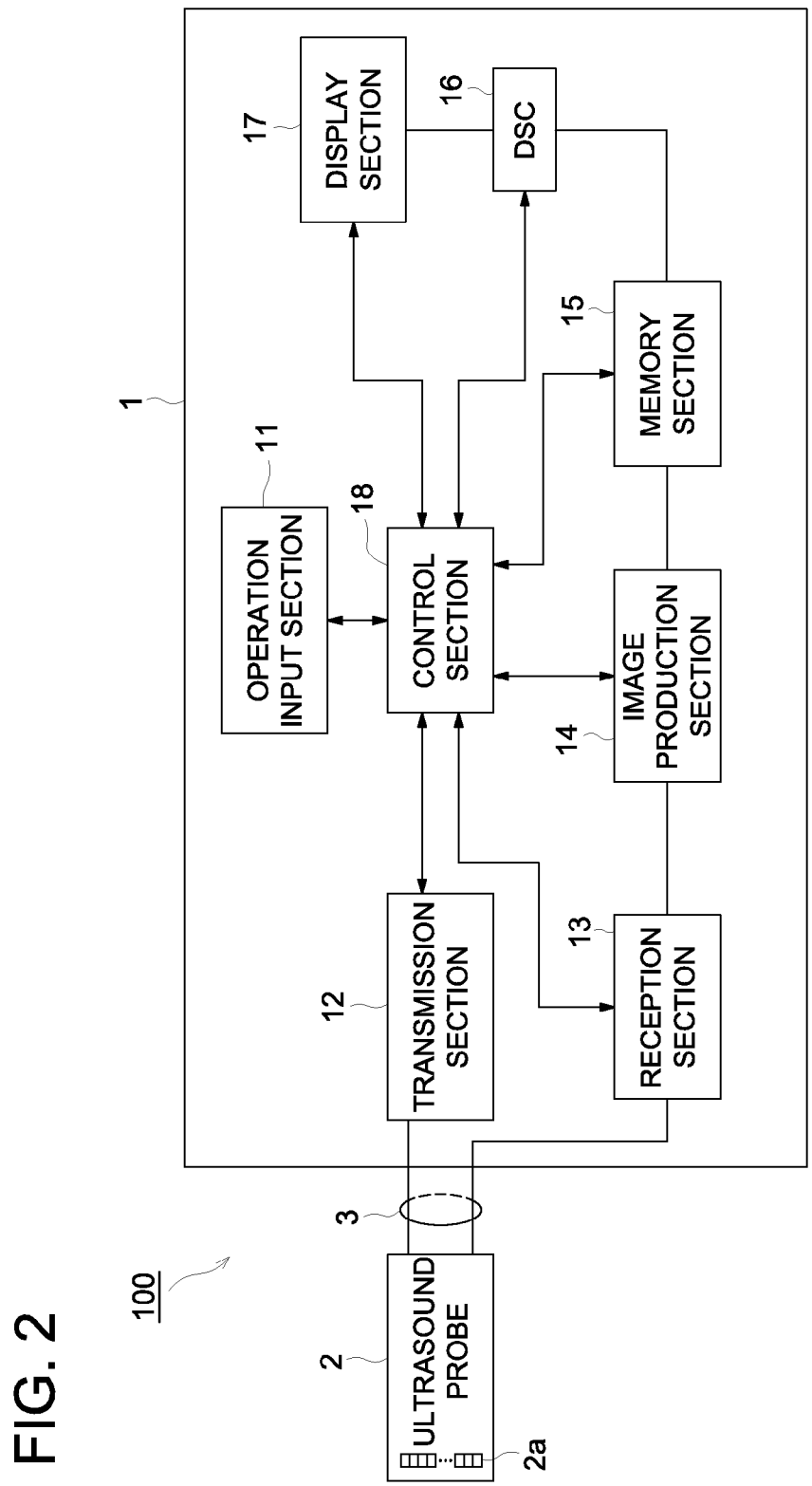
FIG. 2 is a block diagram showing the schematic configuration of the ultrasound diagnostic device.

The ultrasound diagnostic device main body 1 is configured in such a manner that as shown in FIG. 2, for example, an operation input section 11, a transmission section 12, a reception section 13, an image production section 14, a memory section 15, a DSC (Digital Scan Converter) 16, a display section 17, and a control section 18 are provided.

The operation input section 11 is provided with, for example, various types of switch, button, track ball, mouse, and keyboard to input commands to instruct the diagnosis initiation and personal information of a tested subject to output an operation signal to the control section 18.

The transmission section 12 is a circuit in which in accordance with the control of the control section 18, a drive signal being an electrical signal is fed to the ultrasound probe 2 via the cable 3 to allow the ultrasound probe 2 to generate transmission ultrasound. The transmission section 12 is provided with, for example, a clock generation circuit, a delay circuit, and a pulse generation circuit. The clock generation circuit is a circuit to generate a clock signal to determine the transmission timing and the transmission frequency of a drive signal. The delay circuit is a circuit in which with regard to the transmission timing of a drive signal, delay time is set per individual channel corresponding to each transducer 2a, and then the transmission of the drive signal is delayed by the set delay time to converge transmission beams containing transmission ultrasound. The pulse generation circuit is a circuit to generate a pulse signal as a drive signal at a predetermined period.

The transmission section 12 configured in such a manner sequentially switches a plurality of transducers 2a feeding drive signals, with shifting of predetermined numbers thereof per transmission/reception of ultrasound, in accordance with the control of the control section 18 and then drive signals are fed to a plurality of the transducers 2a selected for output to carry out scanning. In the present embodiment, the transmission section 12 selects N continuous transducers $2a_1$-$2a_N$, as actually used transducers, from 192 transducers 2a to transmit ultrasound using the used transducers $2a_1$-$2a_N$. Herein, the used transducers $2a_1$-$2a_N$ are referred to as channels (CHs) 1-N in some cases, respectively. Incidentally, the number of used transducers (the number of openings) is varied based on the depth of a focus point but may be constant.

Figure 3:
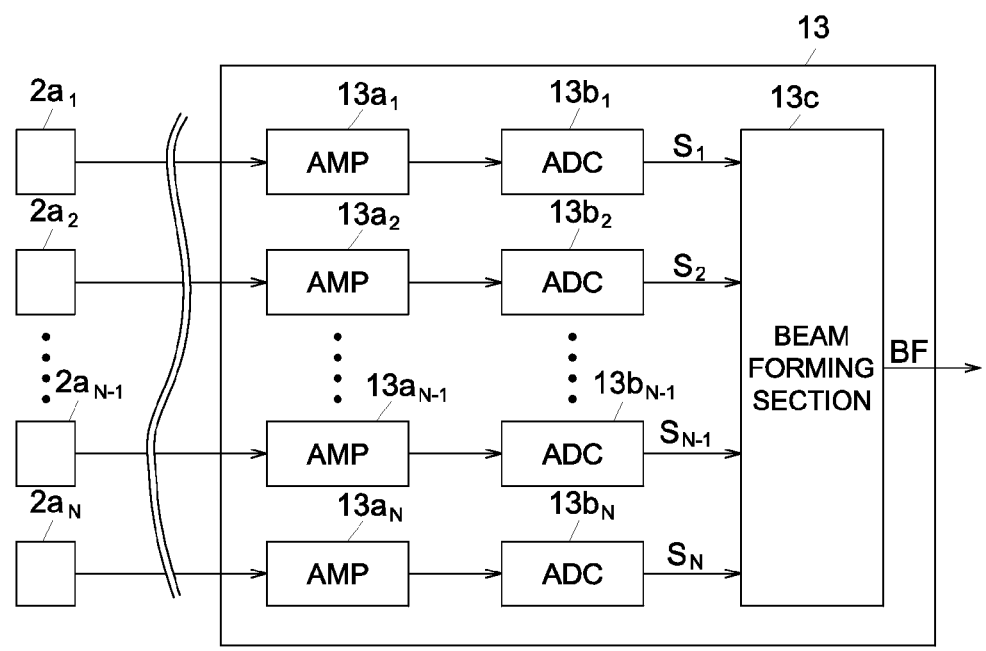
FIG. 3 is a black diagram showing the functional configuration of a reception section.

The reception section 13 is a circuit to receive a reception signal being an electrical signal via the cable 3 from the ultrasound probe 2 in accordance with the control of the control section 18. As shown in FIG. 3, the reception section 13 is provided with, for example, an AMP (Amplifier) 13a (13a$_1$-13a$_N$), an ADC (Analog to Digital Converter) 13b (13b$_1$-13b$_N$), and a beam forming section 13c.

The AMP 13a (13a$_1$-13a$_N$) is a circuit to amplify a reception signal with respect to an individual channel corresponding to each of the used transducers 2a$_1$-2a$_N$ at a given amplification factor preset.

The ADC 13b (13b$_1$-13b$_N$) A/D-converts an amplified reception signal at a predetermined frequency (e.g., 60 MHz) via sampling. The ADCs 13b$_1$-13b$_N$ output A/D-converted reception signals S$_1$-S$_N$ to the beam forming section 13c, respectively.

The beam forming section 13c matches a phase of each of the A/D-converted reception signals S$_1$-S$_N$ by providing each of the A/D converted signals S$_1$-S$_N$ with a delay time and adds these (beam forming). The beam forming section 13c outputs a reception signal having been subjected to beam forming to the image production section 14 as a beam forming signal BF.

Figure 4:
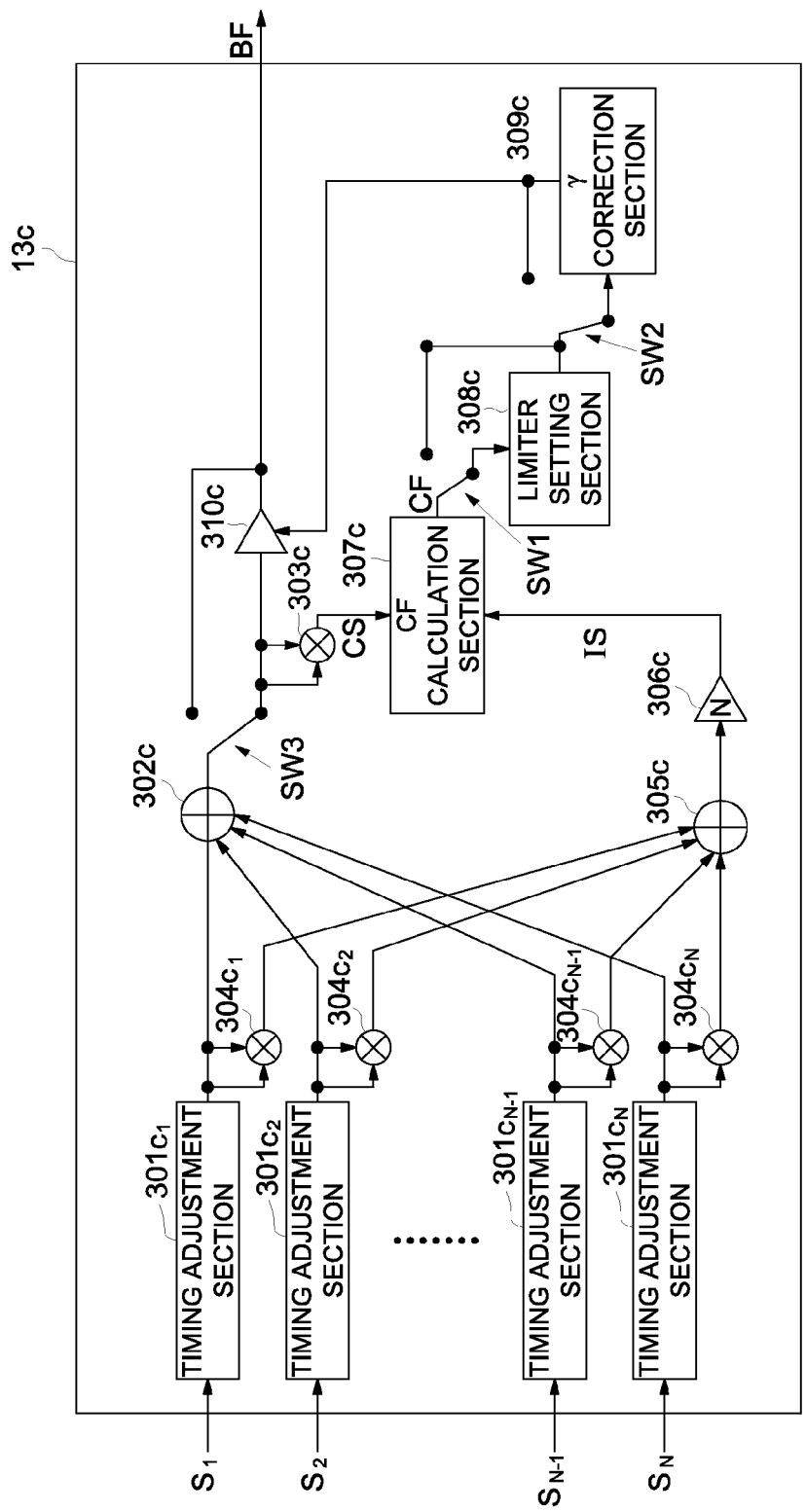
FIG. 4 is a block diagram showing the functional configuration of a beam forming section.

More specifically, as shown in FIG. 4, the beam forming section 13c is provided with a timing adjustment section 301c (301c$_1$-301c$_N$), an adder 302c, a multiplier 303c, a multiplier 304c (304c$_1$-304c$_N$), an adder 305c, a coefficient multiplier 306c, a coherence factor calculation section 307c, a limiter setting section 308c, a γ correction section 309c, a coherence factor multiplier 310c, and switches SW1-SW3.

The timing adjustment section 301c (301c$_1$-301c$_N$) adjusts the output timing of reception signals S$_1$-S$_N$ having been input from the ADCs 13b$_1$-13b$_N$ so that a reception signal delayed by delay amount Δt$_i$ determined per channel based on base time t is output. In this manner, the timing adjustment sections 301c$_1$-301c$_N$ carry out time phase adjustment by providing reception signals S$_1$-S$_N$ each with a delay time.

The adder 302c adds reception signals S$_1$-S$_N$ having been subjected to time phase adjustment by the timing adjustment sections 301c$_1$-301c$_N$ to output a result thereof.

In the present embodiment, as describe above, the timing adjustment section 301c and the adder 302c carry out beam forming of a reception signal. Herein, a reception signal φ(t) after beam forming can be represented by following Expression (2). In Expression (2), t represents a base time; Δt$_i$ represents a delay amount corresponding to each of the channels 1-N; and C$_i$(t+Δt$_i$) represents the signal magnitude of reception signals S$_1$-S$_N$ at the timing delayed by delay amount Δt$_i$ from base time t.

$$\phi(t) = \left| \sum_i C_i(t + \Delta t_i) \right| \quad (2)$$

The multiplier 303c squares a reception signal after phasing addition output from the adder 302c and outputs a result thereof to the coherence factor calculation section 307c as a coherent sum CS. Further, the reception signal after beam forming output from the adder 302c is also output to the coherence factor multiplier 310c.

On the other hand, the multipliers 304c$_1$-304c$_N$ square reception signals S$_1$-S$_N$ output from the timing adjustment sections 301C$_1$-301C$_N$, respectively, to output results thereof.

The adder 305c adds the output results from the multipliers 304c$_1$-304c$_N$ to output a result thereof.

The coefficient multiplier 306c multiplies the output result from the adder 305c by the number of used transducers to output a result thereof to the coherence factor calculation section 307c as an incoherent sum IS.

The coherence factor calculation section 307c calculates a coherence factor from the coherent sum CS and the incoherent sum IS having been input to output a result thereof as a coherence factor CF. The coherence factor indicates the ratio of a coherent sum to an incoherent sum, serving as an indicator to show whether a reception signal after beam forming is ideal. Namely, the coherence factor shows the degree of an error based on a reception signal after ideal beam forming. In the present embodiment, since the configuration described above is employed, a coherence factor CF (t), being the ratio of a coherent sum CS (t) to an incoherent sum IS (t), can be determined by following Expression (3). Herein, N represents the number of transducers (the number of openings) used.

$$CF(t) = \frac{CS(t)}{IS(t)} = \frac{\left| \sum_i C_i(t + \Delta t_i) \right|^2}{N \sum_i |C_i(t + \Delta t_i)|^2} \quad (3)$$

The limiter setting section 308c as one example of a limiter section inputs a coherence factor CF and corrects the coherence factor CF to a lower limit to be output when the thus-input coherence factor CF is less than the lower limit preset. In the present embodiment, for example, the lower limit can be set at either of "−12 dB" and "−18 dB." Herein, any appropriate value is employable as the lower limit. Further, in the present embodiment, using the switch SW1, the ON/OFF of the function of the limiter setting section 308c can be switched. The switch SW1 can be switched, for example, by a setting operation of the user using the operation input section 11. Thereby, the user can carry out correction depending on the occasion.

The γ correction section 309c as one example of a coherence factor conversion section inputs a coherence factor CF to convert an input value into an output value corresponding thereto to be output. Specifically, in the γ correction section 309c, an input coherence factor CF is dealt as an input value and this value is exponentiated by a correction value (γ) to obtain an output value. In the present embodiment, for example, the correction value (γ) can be set at either of "γ=0.75" and "γ=0.5." Herein, the correction value (γ) is not limited those described above but is preferably set in the range of "0<γ<1."

Figure 5:
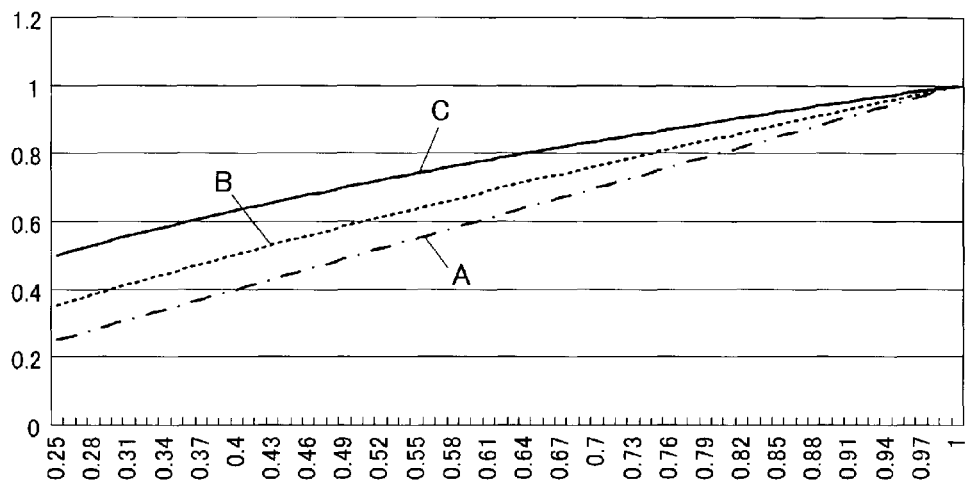
FIG. 5 is a graph showing the relationship between an input value and an output value of a coherence factor.
Figure 6:
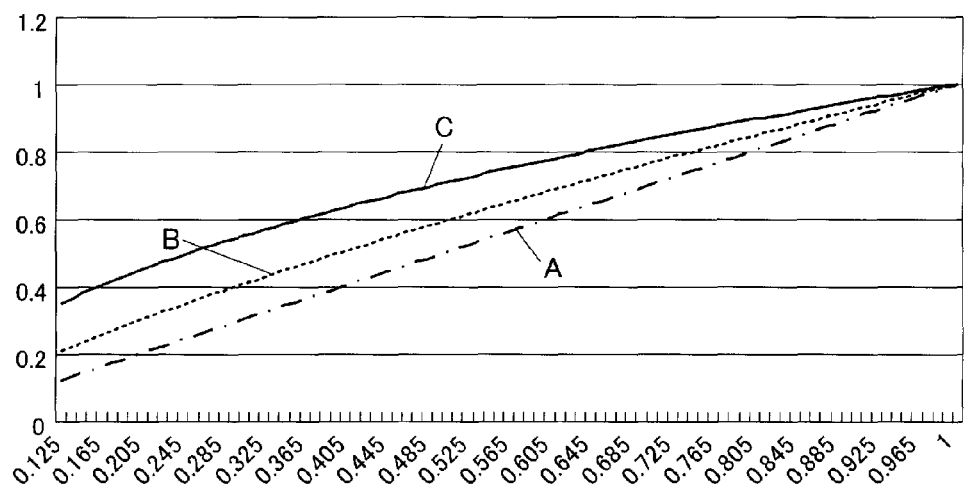
FIG. 6 is a graph showing the relationship between an input value and an output value of a coherence factor.

Here, in the case when a coherence factor CF whose lower limit has been limited to −12 dB by the limiter setting section 308c is dealt as an input value, the relationship between an input value and an output value is shown in FIG. 5, and in the case where a coherence factor CF whose lower limit has been limited to −18 dB by the limiter setting section 308c is dealt as an input value, the relationship between an input value and an output value is shown in FIG. 6. In FIG. 5 and FIG. 6 each, the horizontal axis and the vertical axis represent an input value and an output value, respectively. Further, FIG. 5 and FIG. 6, A shows the relationship between an input value and an output value in the case when the correction value (γ) is "γ=1.0," namely, the γ correction section 309c carries out no correction. B shows the relationship between an input value and an output value in the case where the correction value (γ) is "γ=0.75." And, C shows the relationship between an input value and an output value in the case when the correction value (γ) is "γ=0.5."

In this manner, in the present embodiment, a coherence factor input as described above is exponentiated by a correction value (γ), and thereby with respect to an input coherence factor which is smaller, its value can be more raised.

Incidentally, in the present embodiment, a configuration has been employed so that a coherence factor is exponentiated by a predetermined value to obtain an output value nonlinearly. However, for example, a coherence factor may be multiplied by a predetermined value to obtain an output value linearly. Further, a configuration is employable in which a table such as an LUT (Look Up Table) when an output value is uniquely determined corresponding to an input value is utilized. An input value may also be logarithmically calculated to obtain an output value. A configuration is also employable so that an output value for an input value can be set individually with respect to each input value. Further, the relationship of an output value on an input value may be changed depending on the depth of a focus point.

Further, in the present embodiment, using the switch SW2, the ON/OFF of the function of the γ correction section 309c can be switched. The switch SW2 can be switched, for example, by a setting operation of the user using the operation input section 11. Thereby, the user can carry out correction depending on the occasion.

As described above, the limiter setting section 308c and the γ correction section 309c constitute a coherence factor correction section to correct a coherence factor calculated by the coherence factor calculation section so as not to become smaller than a predetermined value.

Figure 15:
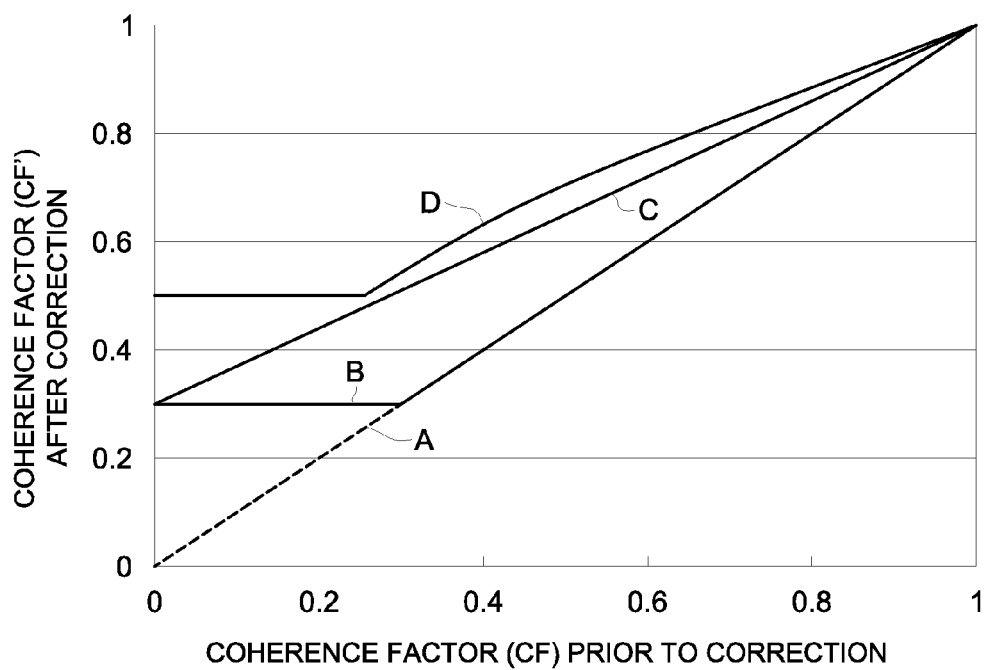
FIG. 15 is a graph showing an example of corrections using a coherence factor.

FIG. 15 is a graph showing one example of the corrections using the coherence factor correction section. The horizontal axis of the graph represents a coherence factor (CF) prior to correction and the vertical axis represents a coherence factor (CF') after correction. In the figure, the line of A represents a coherence factor in the case where no correction was carried out. The line of B represents the case where the lower limit was set at 0.3 by the limiter setting section 308, and the line of C represents the case where a correction was carried out using the expression of CF'=0.7×CF+0.3. In both cases of the line of B and the line of C, a correction is carried out so that even when a coherence factor prior to correction comes closer to zero, a coherence factor after correction is not smaller than a predetermined value (0.3). Further, the line of D shows the case where CF was exponentiated by γ=0.5 and also the lower limit was set at 0.5. In this case, a correction is carried out so that even when a coherence factor prior to correction comes closer to zero, a coherence factor after correction is not smaller than a predetermined value (0.5). In this manner, in any of the corrections shown by the lines of B-D, a coherence factor calculated by the coherence factor calculation section is corrected so as not to become smaller than a predetermined value, and thereby image data with reduced black defects can be produced. However, the lines of B-D have been just exemplified. Any embodiment other than these is employable as long as a correction is carried out so as to realize a value of at least a predetermined value.

Herein, in the present embodiment, a configuration has been employed so that as described above, the limiter setting section 308c and the γ correction section 309c are allowed to selectively function for coherence factor correction. However, a configuration may be employed in which a correction by use of the limiter setting section 308c and the γ correction section 309c is always carried out. Further, a configuration provided with either the limiter setting section 308c or the γ correction section 309c is employable. Still further, in the present embodiment, a configuration has been made so that the lower limit of a coherence factor is limited by the limiter setting section 308c and thereafter a correction is carried out using the γ correction section 309c. However, it is possible that a correction is carried out by the γ correction section 309c and then the lower limit of a coherence factor is limited by the limiter setting section 308c.

The coherence factor multiplier 310c as one example of a signal correction section multiplies a reception signal after beam forming output from the adder 302c by a coherence factor CF output from the coherence factor calculation section 307c, the limiter setting section 308c, or the γ correction section 309c as a coefficient to output a result thereof as a beam forming signal BF to the image production section 14.

In the present embodiment, in such a manner, a reception signal after beam forming can be weighed. Further, when the lower limit of a coherence factor has been limited by the limiter setting section 308c, the weighed amount with respect to a reception signal can be prevented from becoming extremely small, and thereby the magnitude of the reception signal can be ensured to some extent and then occurrence of so-called black defects due to oversuppresion of noise portions can be reduced. Still further, when coherence factor conversion has been carried out by the γ correction section 309c, for a smaller coherence factor, a correction is carried out so as to be further raised, and thereby occurrence of black defects can be effectively reduced.

Further, in the present embodiment, using the switch SW3, the ON/OFF of the function of the coherence factor multiplier 310c can be switched. The switch SW3 can be switched, for example, by a setting operation of the user using the operation input section 11. In other words, in the present embodiment, the beam forming section 13c is configured so that switching whether a reception signal after beam forming is weighed by a coherence factor can be carried out. When the function of the coherence factor multiplier 310c has been turned OFF by the switch SW3, a reception signal after beam forming output from the adder 302c is output as a beam forming signal BF to the image production section 14. Thereby, the user selects whether a coherence factor is applied depending on the occasion, whereby an ultrasound diagnostic image can be acquired.

As shown in FIG. 2, the image production section 14 applies envelope modulation processing and logarithmic amplification to a beam forming signal BF from the reception section 13, followed by dynamic range or gain adjustment for luminance conversion to produce B-mode image data. Namely, the B-mode image data is one in which the intensity of a reception signal is represented by luminance.

The memory section 15 contains a semiconductor memory such as, e.g., a DRAM (Dynamic Random Access Memory) and memorizes B-mode image data transmitted from the image production section 14 on a frame basis. Namely, the memory section 15 can carry out memorizing as ultrasound diagnostic image data constituted based on a frame basis. Then, the thus-memorized ultrasound diagnostic image data is transmitted to the DSC 16 in accordance with the control of the control section 18.

The DSC 16 converts ultrasound diagnostic image data having been received by the memory section 15 into an image signal based on the scanning system of a television signal to be output to the display section 17.

As the display section 17, applicable is a display device such as an LCD (Liquid Crystal Display), a CRT (Cathode-Ray Tube) display, an organic EL (Electronic Luminescence) display, an inorganic EL display, or a plasma display. The display section 17 displays ultrasound diagnostic image data on the display screen in response to an image signal having been output from the DSC 16. Herein, instead of the display device, a printing device such as a printer may be applied.

The control section 18 is constituted of, for example, a CPU (Central Processing Unit), a ROM (Random Only Memory), and a RAM (Random Access Memory), reading out various types of processing program such as a system program memorized in the ROM to be developed on the RAM for central controlling of the operation of each section of the ultrasound diagnostic device 100 in accordance with a developed program.

The ROM contains a nonvolatile memory such as a semiconductor and memorizes a system program corresponding to the ultrasound diagnostic device 100 and various types of processing program executable on the system program, as well as various types of data. These programs are stored in the form of a program code which can be read by the computer, and the CPU sequentially executes operations in accordance with the program code.

The RAM forms a work area to temporarily memorize various types of program executed by the CPU and data relevant to these programs.

EXAMPLES

The present invention will now be detailed with reference to examples but it goes without saying that the present invention is not limited to these examples.

Example 1

Figure 7:
FIG. 7 is a view showing an image acquired by Example 1.

A reception signal having been obtained via transmission/reception of ultrasound with respect to a given phantom having a plurality of wires using the ultrasound diagnostic device 100 according to the present embodiment was subjected to beam forming. A reception signal after beam forming was multiplied by a coherence factor set at −18 dB as the lower limit to be corrected, on the basis of which imaging was carried out. The image is shown in FIG. 7.

Example 2

Figure 8:
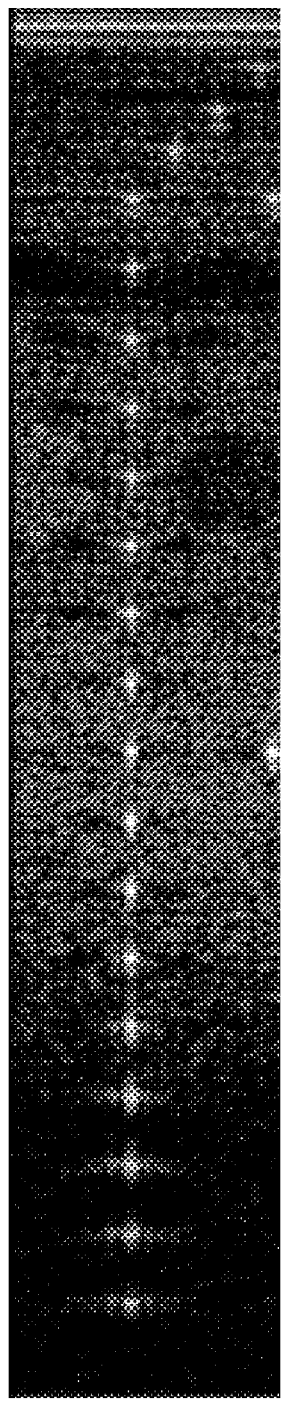
FIG. 8 is a view showing an image acquired by Example 2.

In the same manner, the lower limit was set at −18 dB and then a reception signal after beam forming was multiplied by a corrected coherence factor having been obtained via exponentiation of a correction value ($\gamma=0.75$) to be corrected, on the basis of which imaging was carried out. The image is shown in FIG. 8.

Example 3

Figure 9:
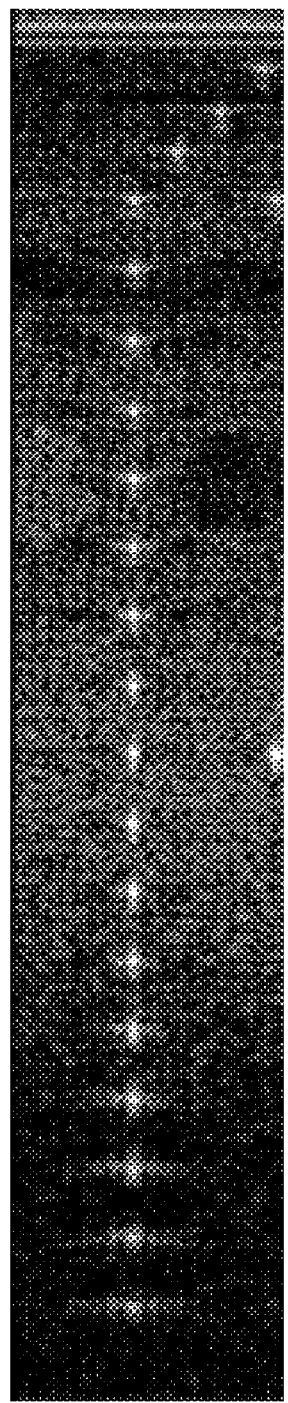
FIG. 9 is a view showing an image acquired by Example 3.

In the same manner, the lower limit was set at −18 dB and then a reception signal after beam forming was multiplied by a corrected coherence factor having been obtained via exponentiation of a correction value ($\gamma=0.5$) to be corrected, on the basis of which imaging was carried out. The image is shown in FIG. 9.

Example 4

Figure 10:
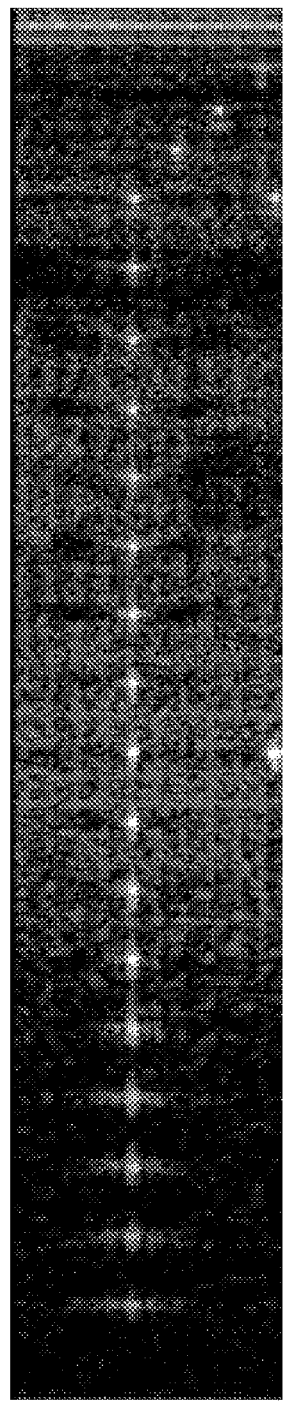
FIG. 10 is a view showing an image acquired by Example 4.

In the same manner, a reception signal after beam forming was multiplied by a coherence factor set at −12 dB as the lower limit to be corrected, on the basis of which imaging was carried out. The image is shown in FIG. 10.

Example 5

Figure 11:
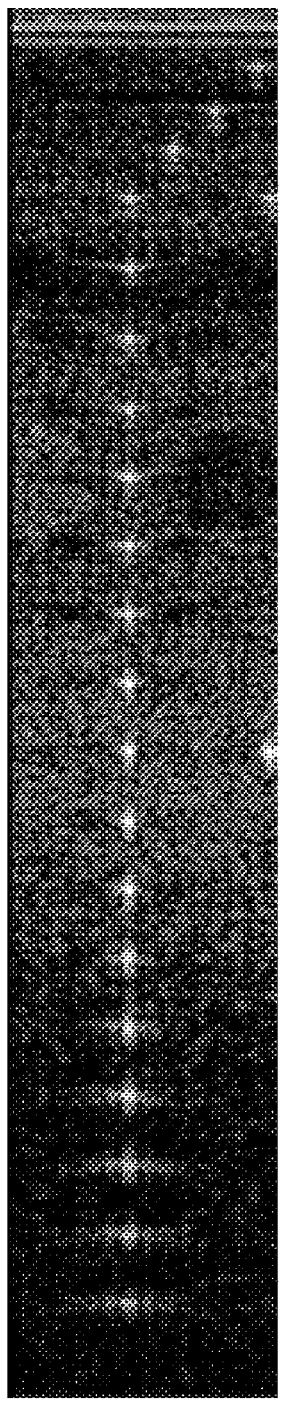
FIG. 11 is a view showing an image acquired by Example 5.

In the same manner, the lower limit was set at −12 dB and then a reception signal after beam forming was multiplied by a corrected coherence factor having been obtained via exponentiation of a correction value ($\gamma=0.75$) to be corrected, on the basis of which imaging was carried out. The image is shown in FIG. 11.

Example 6

Figure 12:
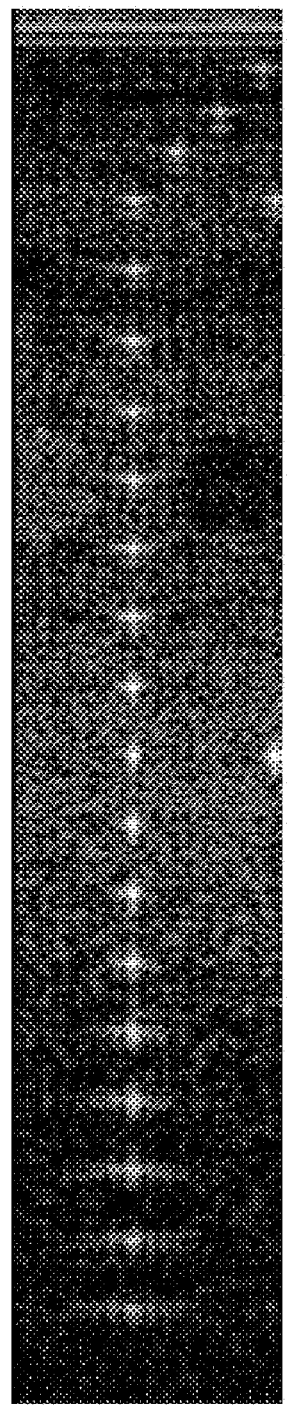
FIG. 12 is a view showing an image acquired by Example 6.

In the same manner, the lower limit was set at −12 dB and then a reception signal after beam forming was multiplied by a corrected coherence factor having been obtained via exponentiation of a correction value ($\gamma=0.5$) to be corrected, on the basis of which imaging was carried out. The image is shown in FIG. 12.

Comparative Example 1

Figure 13:
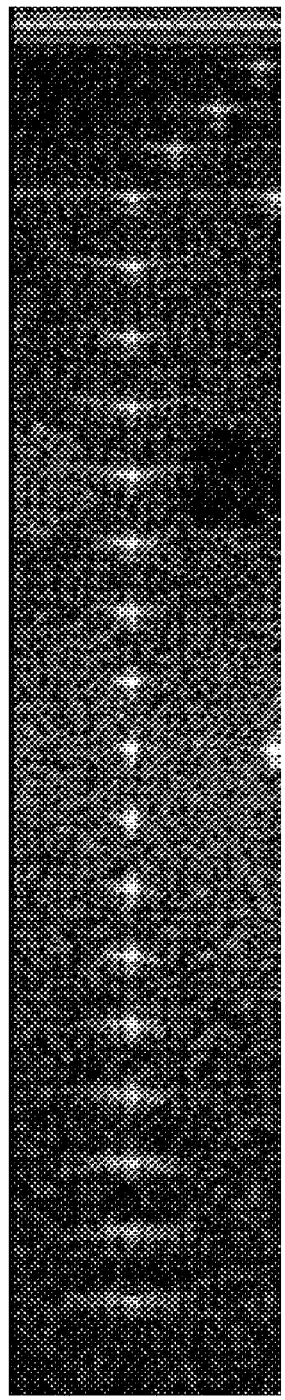
FIG. 13 is a view showing an image acquired by Comparative Example 1.

As Comparative Example 1, a reception signal having been obtained via transmission/reception of ultrasound with respect to the above phantom using the ultrasound diagnostic device 100 according to the present embodiment was subjected to beam forming. A reception signal after beam forming was not weighed by a coherence factor, on the basis of which imaging was carried out. The image is shown in FIG. 13.

Comparative Example 2

Figure 14:
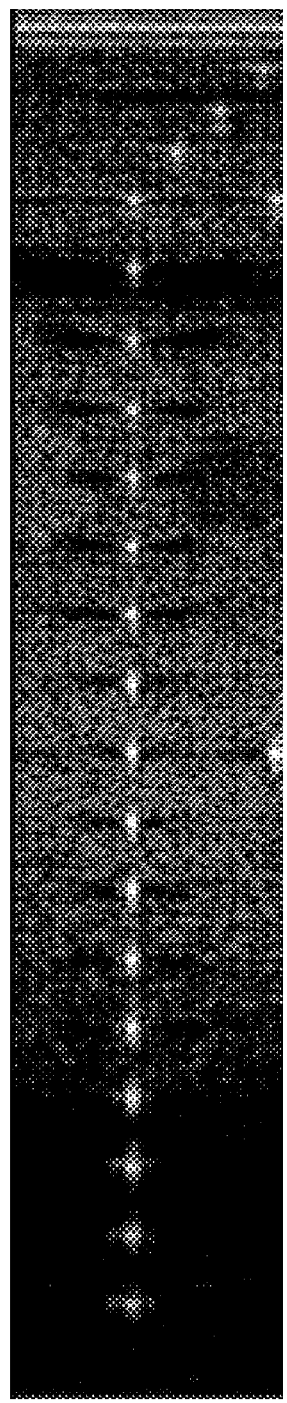
FIG. 14 is a view showing an image acquired by Comparative Example 2.

As Comparative Example 2, a reception signal having been obtained via transmission/reception of ultrasound with respect to the above phantom using the ultrasound diagnostic device 100 according to the present embodiment was subjected to beam forming. A reception signal after beam forming was weighed by a coherence factor in which, however, no lower limit was set or no coherence factor correction was carried out by applying a correction value, on the basis of which imaging was carried out. The image is shown in FIG. 14.

[Results]

In Comparative Example 2, noise is largely suppressed, compared with Comparative Example 1 and thereby an image of enhanced resolution is obtained. Further, in the image by Comparative Example 1, sidelobe is easy to notice. In contrast, in the image by Comparative Example 2, sidelobe is suppressed but the coherence factor is minimized locally, and thereby the degree of suppression is increased, resulting in occurrence of black defects in sidelobe portions. Further, in the image by Comparative Example 2, especially, reception signals in deep portions are extremely weak and also the coherence factor is minimized, whereby black defects are noticeable.

In contrast, in Example 1, an image of enhanced resolution in which black defects in deep portions were reduced to a certain extent was obtained, compared with Comparative Example 2. Further, in the images by Examples 2 and 3, black defects were also largely reduced. Especially, in the image by Exapmle 3, the extent that no black defects in sidelobe portions were noticeable was realized. On the other hand, according to the images by Examples 1-3, it was found that as the correction value decreases, noise occurred.

Further, in the images by Example 4-6, the lower limit of the coherence factor is set higher than in Examples 1-3, and thereby black defects in sidelobe portions and deep portions are further reduced than in the images by Examples 1-3.

As described above, according to the preferred embodiment of the present invention, the ultrasound probe 2 outputs transmission ultrasound to a tested subject by a drive signal using a plurality of transducers $2a_1$-$2a_N$, and also receives reception ultrasound from the tested subject to obtain a reception signal with respect to each of the transducers $2a_1$-$2a_N$. The beam forming section 13c caries out beam forming for the reception signal with respect to each of the transducers $2a_1$-$2a_N$. The image production section 14 produces image data to display an ultrasound diagnostic image, based on a reception signal after beam forming. The coherence factor calculation section 307c calculates a coherence factor CF, which is the ratio of a coherent sum CS to an incoherent sum IS, based on reception signals having been obtained by a plurality of the transducers $2a_1$-$2a_N$. The limiter setting section 308c and the γ correction section 309c correct a coherence factor CF, having been calculated by the coherence factor calculation section 307c, so as not to be smaller than a predetermined value. The coherence factor multiplier 310c multiplies a reception signal after beam forming by a coherence factor having been corrected by at least either of the limiter setting section 308c and the γ correction section 309c as a coefficient to correct the reception signal after beam forming. As a result, the reception signal after beam forming is corrected by applying such a coherence factor and thereby image data having enhanced S/N can be produced. Further, via coherence factor correction, image data, in which black defects generated by applying a coherence factor have been reduced, can be produced. Still further, the coherence factor correction ensures viability and thereby a simple configuration, in which no complicated circuit structure is required, can be realized.

According to the preferred embodiment of the present invention, the limiter setting section 308c corrects a coherence factor CF to the lower limit when the coherence factor is less than a predetermined lower limit. As a result, the coherence factor becomes not less than the lower limit and thereby noise suppression is regulated to some extent and then black defects can be reduced.

According to the preferred embodiment of the present invention, the γ correction section 309c inputs a coherence factor CF to correct the coherence factor so that an output value corresponding to the input coherence factor CF is obtained. As a result, the coherence factor can be changed to a preferable value and thereby image data desirable to the user can be obtained.

Further, according to the preferred embodiment of the present invention, the γ correction section 309c obtains an output value by raising an input coherence factor to the power of γ(0<γ<1). AS a result, as the coherence factor is decreased, correction is carried out so as to be raised and thereby image data in which occurrence of black defects is effectively reduced can be obtained.

Herein, the description in the preferred embodiment of the present invention is one example of the ultrasound diagnostic device according to the present invention, and is not limited thereto. The detailed configuration and the detailed operation of each functional section constituting the ultrasound diagnostic device are also appropriately modified.

Further, in the present embodiment, a reception signal was sampled and A/D-converted, followed by beam forming. However, a configuration is employable in which no A/D conversion is cathed out and then beam forming is performed.

The preferred embodiment makes it possible that using a simple configuration, image data in which black defects are reduced and S/N is improved can be produced.

What is claimed is:

1. An ultrasound diagnostic device comprising:
an ultrasound probe which transmits ultrasound toward a tested subject by a plurality of transducers by a driving signal and obtains a received signal for each of the transducers by receiving a reflective ultrasound wave from the tested subject;
a beam forming circuit which matches a phase of the received signal for each of the transducers and adds the received signals having been subjected to phase matching; and
a processor which generates image data for displaying an ultrasound diagnostic image based on a plurality of the received signals having been subjected to the adding;
wherein the beam forming circuit comprises:
a coherence factor calculation section which calculates a coherence factor which represents a ratio of a coherent sum to an incoherent sum, based on the received signal obtained by the plurality of transducers;
a coherence factor correction section which corrects the coherence factor calculated by the coherence factor calculation section by performing a correction calculation process on the coherence factor to calculate a corrected coherence factor value; and
a signal correction section which corrects each of the received signals having been subjected to the adding by multiplying each of the received signals having been subjected to the adding by the corrected coherence factor value calculated by the coherence factor correction section as a coefficient,
wherein the processor generates the image data for displaying the ultrasound diagnostic image based on each received signal corrected by the signal correction section; and
wherein the coherence factor correction section includes a limiter section which, when the coherence factor is less than a predetermined value, corrects the coherence factor to at least the predetermined value.

2. The ultrasound diagnostic device described in claim 1, wherein the coherence factor calculation section calculates the coherence factor CF(t) by the following expression (1):

$$CF(t) = \frac{\left|\sum_i C_i(t+\Delta t_i)\right|^2}{N \sum_i |C_i(t+\Delta t_i)|^2} \quad (1)$$

where N represents a number of the plurality of transducers and is a positive integer number;
t represents an arbitrary reference time;
i represents a channel of one arbitrary transducer among the N number of transducers;
$\Delta t_i$ represents a delay amount determined for the channel i; and
$C_i(t+\Delta t_i)$ represents a received signal at a time obtained by adding the time t with the delay $\Delta t_i$.

3. An ultrasound diagnostic device comprising:
an ultrasound probe which transmits ultrasound toward a tested subject by a plurality of transducers by a driving signal and obtains a received signal for each of the transducers by receiving a reflective ultrasound wave from the tested subject;

a beam forming circuit which matches a phase of the received signal for each of the transducers and adds the received signals having been subjected to phase matching; and a processor which generates image data for displaying an ultrasound diagnostic image based on a plurality of the received signals having been subjected to the adding;

wherein the beam forming circuit comprises:

a coherence factor calculation section which calculates a coherence factor which represents a ratio of a coherent sum to an incoherent sum, based on the received signal obtained by the plurality of transducers;

a coherence factor correction section which corrects the coherence factor calculated by the coherence factor calculation section; and a signal correction section which corrects each of the received signals having been subjected to the adding by multiplying each of the received signals having been subjected to the adding by the coherence factor corrected by the coherence factor correction section as a coefficient, and wherein:

the coherence factor correction section includes a coherence factor conversion section which inputs the coherence factor and corrects the coherence factor so as to obtain an output value corresponding to the input coherence factor;

the coherence factor conversion section obtains the output value by exponentiating the input coherence factor by a value γ which satisfies the following conditional expression: 0<γ<1; and the processor generates the image data for displaying the ultrasound diagnostic image based on each received signal corrected by the signal correction section.

4. The ultrasound diagnostic device described in claim 3, wherein the coherence factor calculation section calculates the coherence factor CF(t) by the following expression (1):

$$CF(t) = \frac{\left|\sum_i C_i(t+\Delta t_i)\right|^2}{N \sum_i |C_i(t+\Delta t_i)|^2} \quad (1)$$

where:

N represents a number of the plurality of transducers and is a positive integer number;

t represents an arbitrary reference time;

i represents a channel of one arbitrary transducer among the N number of transducers;

$\Delta t_i$ represents a delay amount determined for the channel i; and $C_i(t+\Delta t_i)$ represents a received signal at a time obtained by adding the time t with the delay $\Delta t_i$.

5. The ultrasound diagnostic device described in claim 3, wherein the coherence factor correction section is configured to be able to set an output value for each input coherence factor.

6. The ultrasound diagnostic device described in claim 1, further comprising a switch to switch ON/OFF of functioning of the coherence factor correction section.

7. The ultrasound diagnostic device described in claim 3, further comprising a switch to switch ON/OFF of functioning of the coherence factor correction section.

8. The ultrasound diagnostic device described in claim 1, further comprising a switch to switch ON/OFF of functioning of the limiter section.

9. The ultrasound diagnostic device described in claim 1, wherein:

the coherence factor correction section further includes a coherence factor conversion section which inputs the coherence factor and corrects the coherence factor so as to obtain an output value corresponding to the input coherence factor;

the coherence factor conversion section obtains the output value by exponentiating the input coherence factor by a value γ which satisfies the following conditional expression: 0<γ<1; and the coherence factor correction section performs correction of the coherence factor such that the output value is not less than the predetermined value set by the limiter section.

10. The ultrasound diagnostic device described in claim 1, wherein the coherence factor correction section further includes a coherence factor conversion section which inputs the coherence factor and corrects the coherence factor by multiplying the coherence factor by a second predetermined value so as to obtain an output value corresponding to the input coherence factor.

11. The ultrasound diagnostic device described in claim 1, wherein:

the coherence factor correction section further includes a coherence factor conversion section which inputs the coherence factor and corrects the coherence factor so as to obtain an output value corresponding to the input coherence factor; and the coherence factor conversion section obtains the output value by exponentiating the input coherence factor by a value γ which satisfies the following conditional expression: 0<γ<1.

12. The ultrasound diagnostic device described in claim 10, wherein the limiter section and the coherence factor conversion section are selectively operable such that (i) correction of the coherence factor is performed only by the limiter section, (ii) correction of the coherence factor is performed only by the coherence factor conversion section, or (iii) correction is performed by both of the limiter section and the coherence factor conversion section.

13. The ultrasound diagnostic device described in claim 11, wherein the limiter section and the coherence factor conversion section are selectively operable such that (i) correction of the coherence factor is performed only by the limiter section, (ii) correction of the coherence factor is performed only by the coherence factor conversion section, or (iii) correction is performed by both of the limiter section and the coherence factor conversion section.

14. The ultrasound diagnostic device described in claim 1, wherein the limiter section adds the predetermined value to an input value of the coherence factor to obtain a first corrected coherence factor value, and the coherence factor correction section further includes a coherence factor conversion section which multiplies the first corrected coherence factor value by a second predetermined value so as to obtain an output value, as the corrected coherence factor.

15. The ultrasound diagnostic device described in claim 1, wherein, when the coherence factor is less than the predetermined value, the limiter section corrects the coherence factor to the predetermined value.

\* \* \* \* \*